(12) United States Patent
Williams

(10) Patent No.: US 6,925,856 B1
(45) Date of Patent: Aug. 9, 2005

(54) NON-CONTACT TECHNIQUES FOR MEASURING VISCOSITY AND SURFACE TENSION INFORMATION OF A LIQUID

(75) Inventor: Roger O. Williams, Paradise Valley, AZ (US)

(73) Assignee: EDC Biosystems, Inc., San Jose, CA (US)

( * ) Notice: Subject to any disclaimer, the term of this patent is extended or adjusted under 35 U.S.C. 154(b) by 0 days.

(21) Appl. No.: 10/290,626

(22) Filed: Nov. 7, 2002

Related U.S. Application Data

(60) Provisional application No. 60/346,132, filed on Nov. 7, 2001.

(51) Int. Cl.[7] .................... G01N 11/00; G01N 13/00; G01N 29/10
(52) U.S. Cl. .................. 73/64.48; 73/54.41; 73/64.53; 73/618; 73/620; 73/624; 73/629
(58) Field of Search ........................... 73/54.41, 64.48, 73/64.53, 579, 597, 599, 602, 618, 620, 624, 73/629

(56) References Cited

U.S. PATENT DOCUMENTS

| | | | |
|---|---|---|---|
| 3,903,990 A | 9/1975 | Tannaka | |
| 4,225,951 A | 9/1980 | Menin et al. | |
| 4,308,547 A | 12/1981 | Lovelady et al. | ............. 347/46 |

(Continued)

FOREIGN PATENT DOCUMENTS

| | | | |
|---|---|---|---|
| EP | 0 549 244 | | 6/1993 |
| EP | 0 845 357 | | 6/1998 |
| JP | 2-98651 | * | 4/1990 |

(Continued)

OTHER PUBLICATIONS

Avrameas, S. et al. (1978), "Coupling of Enzymes to Antibodies and Antigens,"*Scandinavia J. of Immunol.* 8(Suppl. 7):7-23.

(Continued)

*Primary Examiner*—Daniel S. Larkin
(74) *Attorney, Agent, or Firm*—Morrison & Foerster LLP

(57) ABSTRACT

A non-contact method for measuring viscosity and surface tension information of a liquid in a first liquid containment structure. The steps of the method include oscillating a free surface of the liquid in the liquid containment structure; detecting wave characteristics of the oscillating free surface; and analyzing the wave characteristics. The oscillating step may be performed by propagating an acoustic wave from an acoustic wave emitter, through said liquid containment structure, towards the free surface. The detecting step may be performed by delivering a series of acoustic pulses at the free surface and detecting acoustic reflections from the free surface as the oscillating free surface relaxes. The analyzing step can be performed by comparing the wave characteristics with a candidate liquid wave characteristics. Prior knowledge and behavior of the selected candidate liquid can thus be imputed to the source or sample liquid. The sample liquid can be one of photoresist, solder or a biological compound. In a variation a method for acoustically ejecting a droplet of a first liquid from a first liquid containment structure comprises measuring viscosity and surface tension information of the first liquid in the first liquid containment structure and directing a variable amount of acoustic energy through the first liquid to cause the droplet ejection wherein the variable amount of acoustic energy is based on the measuring viscosity and surface tension information of the first liquid in the first liquid containment structure. Apparatuses and systems for carrying out the same are included.

22 Claims, 5 Drawing Sheets

U.S. PATENT DOCUMENTS

| | | | |
|---|---|---|---|
| 4,385,255 A | 5/1983 | Yamaguchi et al. | |
| 4,493,795 A | 1/1985 | Nestor, Jr. et al. | |
| 4,512,183 A * | 4/1985 | Alexander | 73/64.48 |
| 4,605,009 A | 8/1986 | Pourcelot et al. | |
| 4,611,486 A * | 9/1986 | Stockhausen | 73/64.48 |
| 4,697,195 A | 9/1987 | Quate et al. | |
| 4,719,476 A | 1/1988 | Elrod et al. | |
| 4,719,480 A | 1/1988 | Elrod et al. | |
| 4,745,419 A | 5/1988 | Quate et al. | |
| 4,748,461 A | 5/1988 | Elrod | |
| 4,749,900 A | 6/1988 | Hadimioglu et al. | |
| 4,751,529 A | 6/1988 | Elrod et al. | |
| 4,751,530 A | 6/1988 | Elrod et al. | |
| 4,751,534 A | 6/1988 | Elrod et al. | |
| 4,782,350 A | 11/1988 | Smith et al. | |
| 4,797,693 A | 1/1989 | Quate | |
| 4,801,950 A | 1/1989 | Frehling | |
| 4,801,953 A | 1/1989 | Quate | |
| 4,867,517 A | 9/1989 | Rawson | |
| 4,959,674 A | 9/1990 | Khri-Yakub et al. | |
| 5,028,937 A | 7/1991 | Khuri-Yakub et al. | |
| 5,041,849 A | 8/1991 | Quate et al. | |
| 5,070,488 A | 12/1991 | Fukushima et al. | |
| 5,074,649 A | 12/1991 | Hamanaka | |
| 5,087,931 A | 2/1992 | Rawson | |
| 5,111,220 A | 5/1992 | Hadimioglu et al. | |
| 5,115,809 A | 5/1992 | Saitoh et al. | |
| 5,121,141 A | 6/1992 | Hadimoglu et al. | |
| 5,122,818 A | 6/1992 | Elrod et al. | |
| 5,142,307 A | 8/1992 | Elrod et al. | |
| 5,163,436 A | 11/1992 | Saitoh et al. | |
| 5,176,140 A | 1/1993 | Kami et al. | |
| 5,191,354 A | 3/1993 | Quate | |
| 5,194,880 A | 3/1993 | Elrod et al. | |
| 5,216,451 A | 6/1993 | Rawson et al. | |
| 5,229,793 A | 7/1993 | Hadimioglu et al. | |
| 5,231,426 A | 7/1993 | Sweet | |
| 5,268,610 A | 12/1993 | Hadimioglu et al. | |
| 5,278,028 A | 1/1994 | Hadimioglu et al. | |
| 5,287,126 A | 2/1994 | Quate | |
| 5,299,578 A | 4/1994 | Rotteveel et al. | |
| 5,305,016 A | 4/1994 | Quate | |
| 5,339,101 A | 8/1994 | Rawson et al. | |
| 5,379,865 A | 1/1995 | Berdich et al. | |
| 5,389,956 A | 2/1995 | Hadimioglu et al. | |
| 5,428,381 A | 6/1995 | Hadimioglu et al. | |
| 5,450,107 A | 9/1995 | Rawson | |
| 5,504,564 A | 4/1996 | Snelling et al. | |
| 5,520,715 A | 5/1996 | Oeftering | |
| 5,541,627 A | 7/1996 | Quate | |
| 5,565,113 A | 10/1996 | Hadimioglu et al. | |
| 5,589,864 A | 12/1996 | Hadimioglu | |
| 5,591,490 A | 1/1997 | Quate | |
| 5,608,433 A | 3/1997 | Quate | |
| 5,612,723 A | 3/1997 | Shimura et al. | |
| 5,629,724 A | 5/1997 | Elrod et al. | |
| 5,631,678 A | 5/1997 | Hadimioglu et al. | |
| 5,669,389 A | 9/1997 | Rotteveel et al. | |
| 5,669,971 A | 9/1997 | Bok et al. | |
| 5,686,945 A | 11/1997 | Quate et al. | |
| 5,692,068 A | 11/1997 | Bryenton et al. | |
| 5,709,737 A | 1/1998 | Malhotra et al. | |
| 5,722,479 A | 3/1998 | Oeftering | |
| 5,798,779 A | 8/1998 | Nakayasu et al. | |
| 5,808,636 A | 9/1998 | Stearns | |
| 5,810,009 A | 9/1998 | Mine et al. | |
| 5,821,958 A | 10/1998 | Lim | |
| 5,877,800 A | 3/1999 | Robinson et al. | |
| 5,912,679 A | 6/1999 | Takayama et al. | |
| 6,003,388 A | 12/1999 | Oeftering | |
| 6,007,183 A | 12/1999 | Horine | |
| 6,015,880 A | 1/2000 | Baldeschwieler et al. | |
| 6,019,814 A | 2/2000 | Horine | |
| 6,029,518 A | 2/2000 | Oeftering | 73/570.5 |
| 6,038,752 A | 3/2000 | Finsterwald et al. | |
| 6,048,050 A | 4/2000 | Gundlach et al. | |
| 6,134,291 A | 10/2000 | Roy et al. | |
| 6,136,210 A | 10/2000 | Biegelsen et al. | |
| 6,142,618 A | 11/2000 | Smith et al. | |
| 6,154,236 A | 11/2000 | Roy et al. | |
| 6,159,013 A | 12/2000 | Parienti | |
| 6,187,211 B1 | 2/2001 | Smith et al. | |
| 6,200,491 B1 | 3/2001 | Zesch et al. | |
| 6,299,272 B1 | 10/2001 | Baker et al. | |
| 6,312,121 B1 | 11/2001 | Smith et al. | |
| 6,336,696 B1 | 1/2002 | Ellson et al. | |
| 6,368,482 B1 | 4/2002 | Oeftering et al. | |
| 2002/0037359 A1 | 3/2002 | Mutz et al. | |
| 2002/0037375 A1 | 3/2002 | Ellson et al. | 427/600 |
| 2002/0037527 A1 | 3/2002 | Ellson et al. | |
| 2002/0037579 A1 | 3/2002 | Ellson et al. | |
| 2002/0042077 A1 | 4/2002 | Ellson | |
| 2002/0061258 A1 | 5/2002 | Mutz et al. | 422/53 |
| 2002/0061598 A1 | 5/2002 | Mutz et al. | 436/180 |
| 2002/0064808 A1 | 5/2002 | Mutz et al. | |
| 2002/0064809 A1 | 5/2002 | Mutz et al. | |
| 2002/0085063 A1 | 7/2002 | Mutz et al. | |
| 2002/0086319 A1 | 7/2002 | Ellson et al. | |
| 2002/0090720 A1 | 7/2002 | Mutz et al. | |
| 2002/0094582 A1 | 7/2002 | Williams et al. | |
| 2002/0142286 A1 | 10/2002 | Mutz et al. | |
| 2002/0155231 A1 | 10/2002 | Ellson et al. | |

FOREIGN PATENT DOCUMENTS

| | | | |
|---|---|---|---|
| WO | WO 01/36959 | * | 5/2001 |
| WO | WO 02/24323 | | 3/2002 |
| WO | WO 02/24324 | | 3/2002 |
| WO | WO 02/24325 | | 3/2002 |
| WO | WO 02/26394 | | 4/2002 |
| WO | WO 02/26756 | | 4/2002 |
| WO | WO 02/44319 | | 6/2002 |
| WO | WO 02/47075 | | 6/2002 |
| WO | WO 02/66713 | | 8/2002 |

OTHER PUBLICATIONS

Cinbus, C. (1992): "Noncontacting Techniques For Measuring Surface Tension of Liquids," A Dissertation Submitted to the Department of Electrical Engineering and the Committee on Graduate Studies of Stanford University in Partial Fulfillment of the Requirements for the Degree of Doctor of Philosophy. pp. 1-192.

DeLuca, D. (1982), "Immunofluorescence Analysis," Chapter 7 In Antibody as a Tool, The Applications of Immunochemistry Marchalonis, J.J. and Warr, G.W. eds., John Wiley & Sons, Ltd., pp. 189-231.

Galfré, G. and Milstein, C. (1981). "Preparation of Monoclonal Antibodies: Strategies and Procedures," Chapter 1 In Methods in Enzymology vol. 73, Academic Press, Inc. pp. 3-46.

Goldmann, T. and Gonzalez, J. S. (2000). "DNA-Printing: Utilization of a Standard Inkjet Printer for the Transfer of Nucleic Acids to Solid Supports,"Journal of Biochemical and Biophysical Methods 42:105-110.

Lemieux, B. et al. (1998). "Overview of DNA Chip Technology,"Molecular Breeding 4:277-289.

Lemmo, A.V. et al. (1997). "Characterization of an Inkjet Chemical Microdispenser for Combinatorial Library Synthesis,"Analytical Chemistry 69(4):543-551.

Mandenius, C.F. et al. (1986). "Reversible and Specific Interaction of Dehydrogenases with a Coenzyme-Coated Surface Continuously Monitored with a Reflectometer,"*Analytical Biochemistry* 157: 283-288.

NASA, Glenn Research Center, (Oct. 2001). "Technology Opportunity: Acoustic Micro-Dispensing," Combustion & Fluids TOP3-00130, located at http://technology.nasa.gov/scripts, visited on Sep. 4, 2002. 2 pages.

NASA, Glenn Research Center, "Acoustic Liquid Manipulation Improves Selective Plating Process," located at: http://technology.nasa.gov/scripts, visited on Sep. 4, 2002, 1 page.

NASA, Glenn Research Center, "Acoustically Enhanced Electroplating Process," Alchemitron Corporation, located at http://technology.nasa.gov/scripts, visited on Sep. 4, 2002, 1 page.

NASA, Lewis Research Center, (Aug. 1998). "Technology Opportunity: The Directional Electrostatic Accretion Process," Materials & Structures MS-200-1, located at: http://technology.nasa.gov/scripts, visited on Sep. 4, 2002, 2 pages.

NASA, Lewis Research Center, (Aug. 1998), "Technology Opportunity: Liquid Manipulation by Acoustic Radiation Pressure," Combustion & Fluids CF-070-1, located at:http://technology.nasa.gov/scripts, visited on Sep. 4, 2002, 2 pages.

Rodwell, J.D. and McKearn, T.J. (1985). "Linker Technology: Antibody-Mediated Delivery Systems,"*BIO/TECHNOLOGY* 3:889-894.

Southern, E.M. and Maskos, U. (1990). "Support-Bound Oligonucleotides,"*Chemical Abstracts* 113(17):835, Abstract No. 152979r.

\* cited by examiner

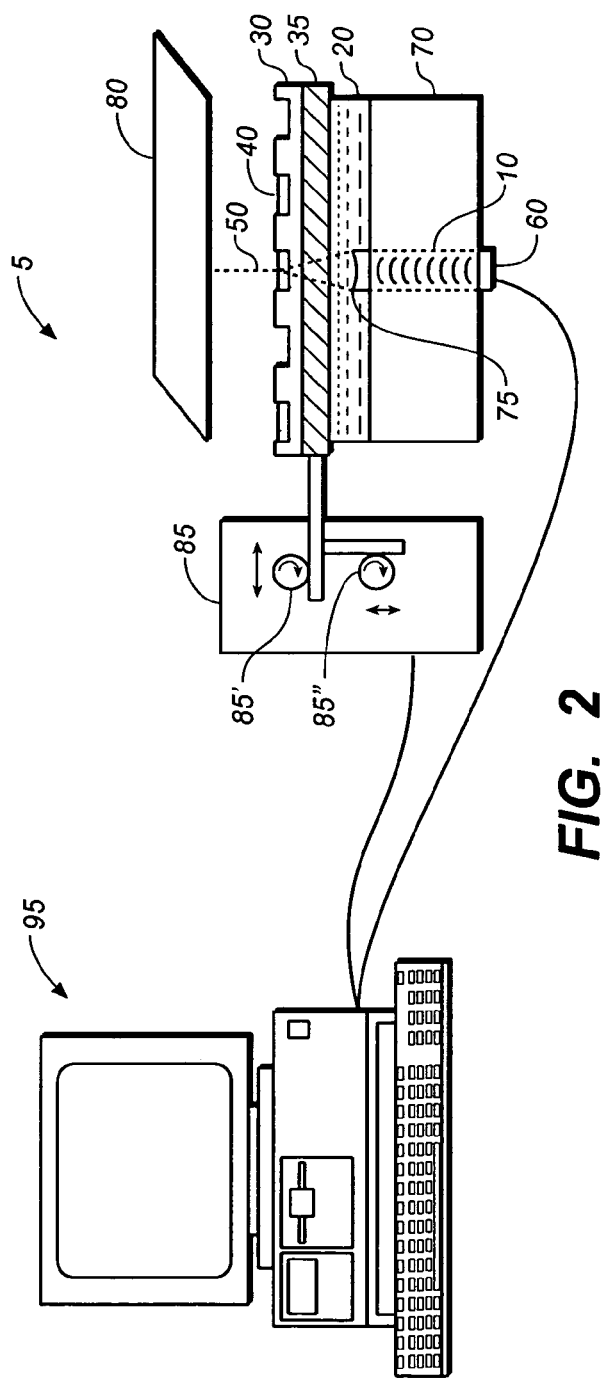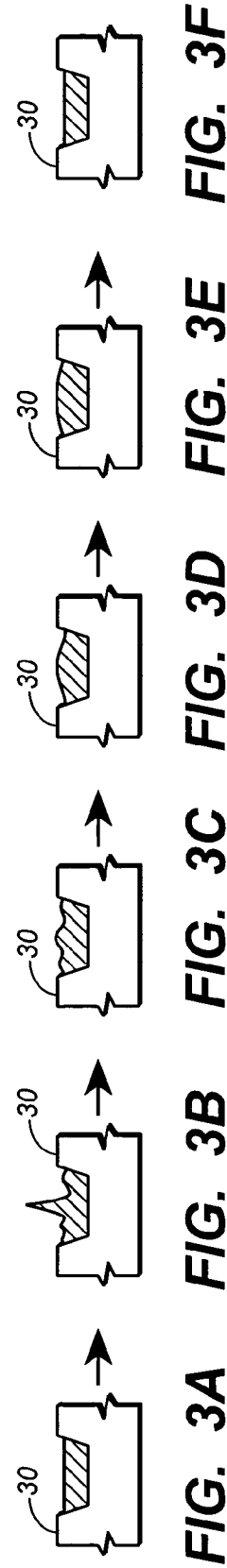

NON-CONTACT TECHNIQUES FOR MEASURING VISCOSITY AND SURFACE TENSION INFORMATION OF A LIQUID

FIELD OF THE INVENTION

The present invention relates to methods for measuring viscosity and surface tension information of a fluid without contacting the fluid. In particular, the present invention relates to measuring viscosity and surface tension information of liquid using acoustic energy.

BACKGROUND

Many methods for the precision transfer and handling of fluids are known and used in a variety of commercial and industrial applications. The presently burgeoning industries of the biotechnology and biopharmaceuticals are particularly relevant examples of industries requiring ultra-pure fluid handling and transfer techniques.

Various current fluid transfer methods require contacting the fluid with a transfer device, e.g., a pipette, a pin, or the like. Such contact methods dramatically increase the likelihood of contamination. Many biotechnology procedures, e.g., polymerase chain reaction (PCR), have a sensitivity that results in essentially a zero tolerance for contamination. Thus, non-contact methods for fluid transfer are desirable.

An exemplary non contact method for ejecting liquid droplets to a target location is described in U.S. application Ser. No. 09/735,709 filed Dec. 12, 2000 entitled "Acoustically Mediated Fluid Transfer Methods And Uses Thereof" and incorporated by reference in its entirety. This fine acoustic liquid ejection technique, however, may be improved by compensating for liquids having varying surface tension and viscosity values. It has been observed that such an acoustic liquid ejector can be limited or adversely affected by varying viscosity and surface tension values of the source liquid to be transferred. Indeed, volume and trajectory of droplet ejection depend upon the acoustic stimuli as well as the viscosity and surface tension of the liquid to be transferred. If the viscosity and surface tension are unknown, then the volume and trajectory of the transferred fluid may vary in an unknown manner. However, with knowledge of the viscosity and surface tension properties of each source, liquid, the acoustic stimuli used to transfer small amounts of fluid may be adjusted accordingly, improving the accuracy and precision of the transfer of that fluid. Thus, it would be advantageous to determine the viscosity and surface tension properties of each fluid prior to ejection. It is also desirable to determine this product in a manner that is easily automated.

Examples of conventional methods for measuring the viscosity of a fluid include capillary tube and rotary viscometers. These techniques require direct contact with the liquid to be measured which may introduce contamination when making multiple measurements.

Examples of conventional methods for measuring surface tension include: sessile drop, pendant drop, maximum bubble pressure, capillary height, the Du Noüy ring, and the Wilhelmy plate methods. All of these techniques have the disadvantage of requiring contact with the fluid or removal of a sample of the fluid.

Examples of non-contact methods of measuring surface tension of sea water are described in Can Cinbis, "Noncontact Techniques for Measuring Surface Tension of Fluids," Doctoral Thesis, Stanford University, 1992. A first method involves measuring the water surface displacement caused by the radiation pressure associated with an acoustic pulse. The displacement is measured with a confocal optical microscope. The surface tension of the liquid is calculated from the measured values. The second method utilizes two ultrasonic transducers: the first transducer generates a wave and the second transducer measures the amplitude of the transient capillary wave a distance from the first transducer. The surface tension is calculated from the measured values. The technique, however, does not provide viscosity information.

None of the above described methods provide a non-contact method to measure viscosity and surface tension information as described herein.

SUMMARY OF THE INVENTION

The present invention includes a non-contact method for measuring viscosity and surface tension information of a first liquid in a first liquid containment structure. The steps of the method include oscillating a free surface of the first liquid in the first liquid containment structure; detecting first liquid wave characteristics of the oscillating free surface; and analyzing the first liquid wave characteristics for the information. The oscillating step may be performed by propagating an acoustic wave from an acoustic wave emitter, through said liquid containment structure, towards the free surface. The detecting step may be performed by delivering a series of acoustic pulses at the free surface and detecting acoustic reflections from the free surface as the oscillating free surface relaxes. The series of acoustic pulses can be synchronously phased and be emitted by the acoustic wave emitter used to cause the free surface to oscillate. The reflections may also be detected by the acoustic wave emitter used to cause the free surface to oscillate.

In a variation of the present invention, the acoustic wave emitter comprises only one piezoelectric transducer for generation and detection of acoustic energy waves. The emitter can be moveable relative to the containment structure and the containment structure can be detachable from the emitter. The containment structure in one variation of the present invention is a multi-well plate.

In another variation of the present invention, the analyzing step includes comparing the first liquid wave characteristics with a candidate liquid wave characteristics. An attribute of the first liquid wave characteristics can be compared to a corresponding attribute of the candidate liquid wave characteristics. In one variation of the present invention, the attribute is a $\Delta t$ defined by the time difference between an upper peak maxim value and lower peak maxim value of the first liquid wave characteristics. The first liquid can be but is not limited to: photoresist, solder, or a biological compound.

In another variation of the present invention, a method for acoustically ejecting a droplet of a first liquid from a first liquid containment structure comprises (1) measuring viscosity and surface tension information of the first liquid in the first liquid containment structure; and (2) directing a variable amount of acoustic energy through the first liquid to cause the droplet ejection wherein the variable amount of acoustic energy is based on the measuring viscosity and surface tension information of the first liquid in the first liquid containment structure. The measuring viscosity and surface information may be performed as described in any one of the above embodiments.

In another variation of the present invention, an apparatus for measuring viscosity and surface tension information of a first liquid in a first liquid containment structure comprises an acoustic energy emitter configured to deliver a first acoustic energy pulse to disturb a free surface of the first liquid in the first liquid containment structure causing said free surface to oscillate. The emitter is further configured to deliver a series of acoustic energy pulses at the oscillating free surface while the oscillating free surface is relaxing. The acoustic energy emitter is further configured to detect wave characteristics of the oscillating free surface by detecting echo signals from the series of energy pulses reflecting off the oscillating free surface. The acoustic wave emitter may be configured to deliver an acoustic ejecting pulse sufficient to eject one or more droplets of liquid from said first liquid. The acoustic energy emitter, in one variation, comprises one and only one piezoelectric element to generate and detect acoustic energy to and from the free surface of said first liquid.

In another variation of the present invention, a system for acoustically ejecting a droplet of liquid from a first liquid containment structure comprises an apparatus as recited above. The system may further comprise a stage for supporting the liquid containment structure wherein the stage is moveable and or detachable relative to the acoustic energy emitter.

BRIEF DESCRIPTION OF THE DRAWINGS

FIG. 2 is a schematic diagram illustrating a system for acoustically moving a portion of source liquid in a source liquid containment structure.

FIGS. 3a–3f illustrate an oscillating free surface of a source liquid in a source liquid containment structure relaxing over time.

DETAILED DESCRIPTION OF THE INVENTION

The present invention relates to methods of measuring viscosity and surface tension information of a liquid without contacting the liquid and in particular, to methods of measuring surface tension and viscosity information of the liquid using acoustic energy.

Figure 1A:
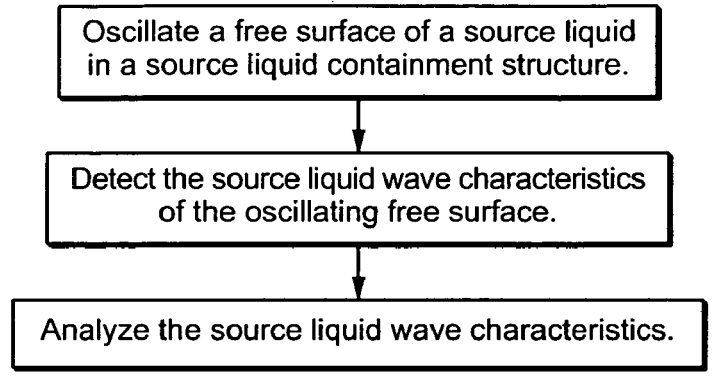
FIG. 1a is a block diagram illustrating the steps performed in one embodiment of the present invention to measure viscosity and surface tension information of a source liquid.
Figure 1B:
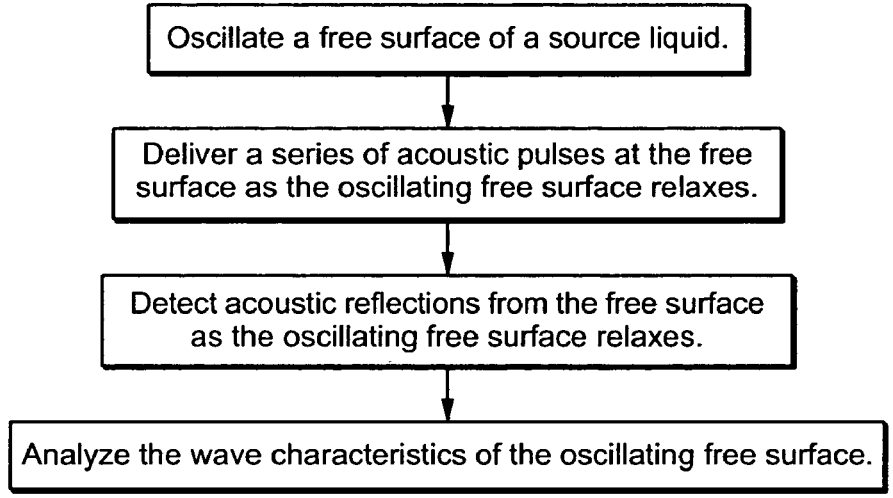
FIG. 1b is a block diagram illustrating the steps performed in another embodiment of the present invention to measure viscosity and surface tension information of a source liquid.

With reference to FIG. 1a, the method of the present invention includes the following steps: (1) oscillate a free surface of a first or source liquid, (2) detect the source liquid wave characteristics of the oscillating free surface and (3) analyze the source liquid wave characteristics. As indicated in FIG. 1b, one embodiment of the present invention provides that the detecting step comprises delivering a series of acoustic pulses at the oscillating free surface as the oscillating free surface relaxes and detecting acoustic reflections from the oscillating free surface as it relaxes. Additionally, the step of analyzing the source liquid wave characteristics may include comparing an attribute of the wave profile of the decaying oscillating free surface of the source liquid with a candidate liquid attribute. The attribute may be, for example, a curve and an curve fitting algorithm may be employed to match the measured source liquid with a candidate liquid having known properties. Accordingly, the present invention provides a method for measuring viscosity and surface tension information without contacting the source liquid.

By viscosity and surface tension information it is meant a measurement of a combination (e.g., a product) of viscosity and surface tension of a liquid. As used hereinafter, viscosity and surface tension information is not intended to mean one and only one of viscosity and surface tension. However, this is not to say that the viscosity and surface tension information measured in accordance with the present invention may not be used in combination with additional knowledge to calculate one of the viscosity and surface tension. While further details, applications, and variations of the measurement technique of the present invention are described hereinafter, the invention is not intended to be limited to these exemplary constructs and techniques. Rather, the invention is intended to be limited only to that covered in the appended claims.

Oscillating a Free Surface of a First Liquid

As indicated above, the first step of the method of the present invention includes oscillating a free surface of a first or source liquid whose viscosity and surface tension product is to be measured. Preferably, an acoustic energy wave is focused at or near the free surface of the source liquid to urge the free surface upwards to form a temporary mound. The acoustic energy wave should be sufficient to urge or disturb the free surface upwards, but, the acoustic energy wave should not exceed a threshold value which would cause liquid to be ejected. However, the threshold value can vary widely and depends on a number of other factors as discussed in copending U.S. application Ser. No. 09/735,709 filed Dec. 12, 2000 entitled "Acoustically Mediated Fluid Transfer Methods And Uses Thereof" hereby incorporated by reference.

An exemplary system 5 to perform the method of the present invention is shown in FIG. 2. It includes at least one acoustic wave emitter 60 in electrical communication with a computer 95. During operation the acoustic liquid deposition emitter 60 generates an acoustic wave or beam 10 that can be propagated through an optional wave channel 70. The acoustic wave can be focused by lens 75 prior to propagating through coupling fluid 20 to optimize the energy of the acoustic wave or beam 10 upon the liquid/air interface (free surface) of source fluid 40. The acoustic wave 10 is propagated through a coupling medium 20 after which the wave is transmitted through source fluid containment structure 30 where the wave comes to focus at or near the surface of a pool of source fluid 40 thereby causing the liquid to urge upwards so as to form a mound.

The mound of liquid subsequently oscillates and relaxes until its oscillations can no longer be observed. FIGS. 3a–3f illustrate, in chronological order, oscillations of a free surface of liquid in a containment structure 30.

Examples of source liquid containment structures include single and multi-well plates commonly used in molecular biology applications, capillaries (e.g., capillary arrays), and the like. However, other containers or structures may be used to hold a liquid to be ejected. Notably, the source fluid containment structure 30 is detachably affixed to a movable stage 35. The movable stage 35 is controlled by actuator mechanism 85 which contains a horizontal actuator 85' or a vertical actuator 85" or a combination of the two actuators to control the movement of the stage 35 in both the vertical and horizontal directions. The actuator 85 is typically in communication with computer 95 which controls the movement of the stage to select a source fluid 40 or to adjust focusing of the acoustic wave or beam 10 upon the source fluid 40. The computer may have implemented thereon various algorithms to adjust the focal length and energy of the acoustic wave emitter as well as control and manage the location of the acoustic wave emitter relative to a particular source fluid present in or on a source fluid containment structure. Accordingly, the system may be used to provide acoustic stimuli to cause the free surface to oscillate such that the surface tension and viscosity value may be determined. The system also may be used to cause a droplet to be ejected from the liquid pool as described in the above referenced copending patent application.

In a preferred embodiment, a piezoelectric transducer is employed as an acoustic wave emitter. In one embodiment, a piezoelectric transducer comprises a flat thin piezoelectric element, which is constructed between a pair of thin film electrode plates. As is understood by those of skill in the art, when a high frequency and appropriate magnitude voltage is applied across the thin film electrode plates of a piezoelectric transducer, radio frequency energy will cause the piezoelectric element to be excited into a thickness mode oscillation. The resultant oscillation of the piezoelectric element generates a slightly diverging acoustic beam of acoustic waves. By directing the wave or beam onto an appropriate lens having a defined radius of curvature (e.g., a spherical lens, or the like), the acoustic beam can be brought to focus at a desired point. Acoustic energy is delivered for a short period of time to form the mound. A suitable short period of time is from 1 to 30 $\mu s$.

In one embodiment, a computer sends an analog voltage pulse to the piezoelectric transducer by an electrical wire. The voltage pulse can be controlled, for example, by a MD-E-201 Drive Electronics manufactured by Microdrop, GmbH, Muhlenweg 143, D-22844 Norderstedt, Germany. The electronics can control the magnitude and duration of the analog voltage pulses, and also the frequency at which the pulses are sent to the piezoelectric transducer. Each voltage pulse causes the generation of an acoustic wave from the piezoelectric transducer, which in turn is propagated through a coupling medium and into or through the source fluid thereby impinging on the surface of the source fluid. Such acoustic waves may be generated to urge the surface of the source fluid into an excited oscillating state.

The piezoelectric transducer may be in the form of a flat crystal disk, or other crystal designs, e.g., square, perforated disk, and the like. In a preferred embodiment, the piezoelectric transducer is a flat disk. Because many electronic circuits are designed for a 50 $\Omega$ (ohm) load, it is presently preferred to employ a 50 $\Omega$ transducer. While the materials for the piezoelectric element may vary greatly, a preferred material is a Navy Type I piezoelectric material disk element having a diameter D=0.039 inch or D=0.991 mm. Other shapes of piezoelectric crystals are also contemplated for use in the practice of the present invention.

Detecting of Oscillations in the Fluid Surface

Detection of the oscillating free surface of the source fluid is preferably performed using acoustic waves. For example, a series of acoustic pulses may be directed at the oscillating free surface as it relaxes. The pulses may be synchronously phased. The echoes or reflections of the pulses from the oscillating free surface are detected and recorded. In this manner, data is generated for each source or sample liquid.

Figure 4A:
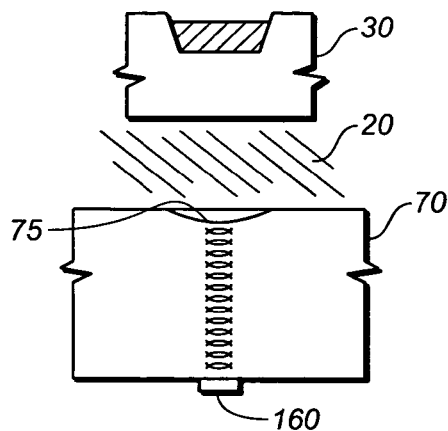
FIG. 4a is a schematic diagram illustrating an acoustic energy emitter having one piezoelectric element.

Various emitter configurations can be employed to carry out the detection step. An exemplary configuration is shown in FIG. 4a wherein a single transducer 160 is provided to emit and detect acoustic waves off the oscillating free surface. The emitter 160 may also be used for the oscillating step described above.

Figure 4B:
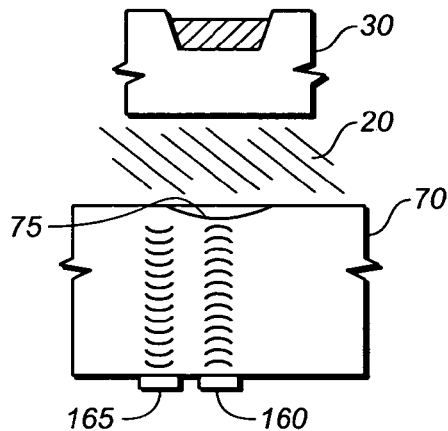
FIG. 4b is a schematic diagram illustrating an acoustic energy apparatus having two piezoelectric elements.
Figure 4C:
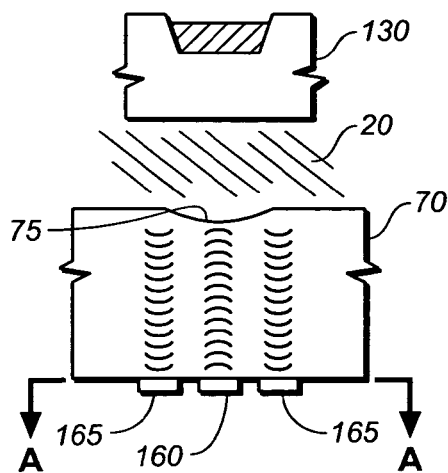
FIG. 4c is a schematic diagram illustrating an acoustic wave emitter having a central piezoelectric element and a second piezoelectric element circumferentially surrounding the first element.
Figure 4D:
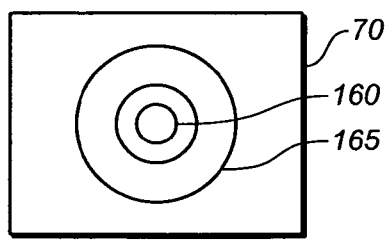
FIG. 4d is a bottom view of the apparatus illustrated in FIG. 4c taken along A—A.

FIG. 4b illustrates another embodiment having a secondary piezoelectric transducer 165. The secondary piezoelectric transducer 165 can be employed to detect the oscillations of the free surface of the fluid. The secondary piezoelectric transducer may be adjacent to a primary transducer 160 or it may be toroidal-shaped as shown in FIGS. 4c and 4d. Thus, a wide range of transducer configurations may be employed to direct and detect acoustic energy from the free surface. Additionally, at least one of the transducers may be used to deliver energy sufficient to eject a droplet of source liquid.

Detection may also be performed by optically observing the oscillating free surface of the source liquid. Optical detectors contemplated for use with the present invention include but are not limited to a camera, a photoelectric cell, and the like. For example, a laser or other light source can be directed at the surface of a source pool, and the scattering of the laser or other light caused by the oscillating free surface can be detected by one or more photoelectric cells coupled to a computer. Other optical detection methods known to those of skill in the art or developed in the future may be employed in order to detect the oscillating surface of the source liquid.

Analyzing the Source Liquid Wave Characteristics

Figure 5A:
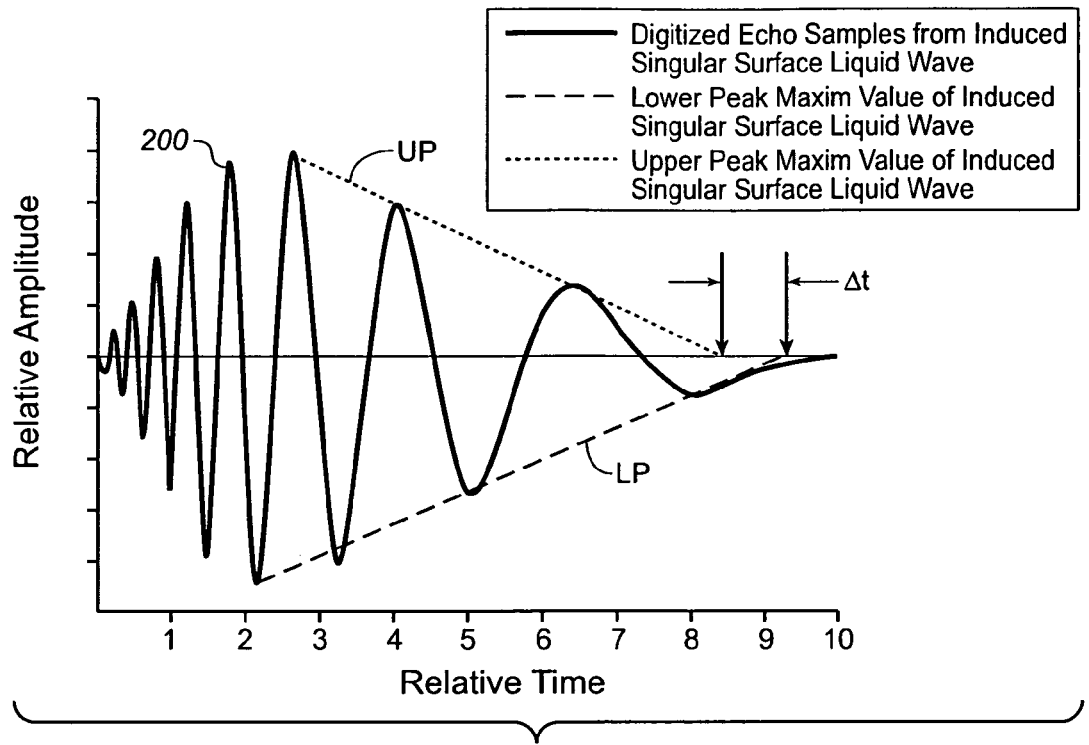
FIGS. 5a–5c are graphs showing echo data of an oscillating free surface of a liquid as the oscillating free surface relaxes.
Figure 5B:
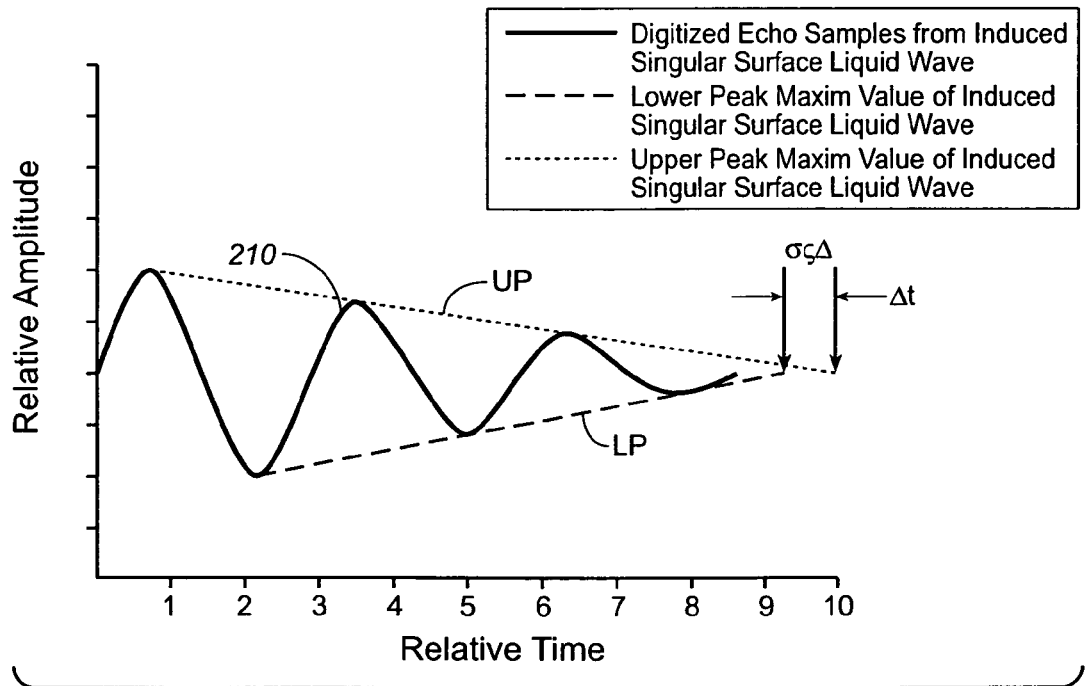
Figure 5C:
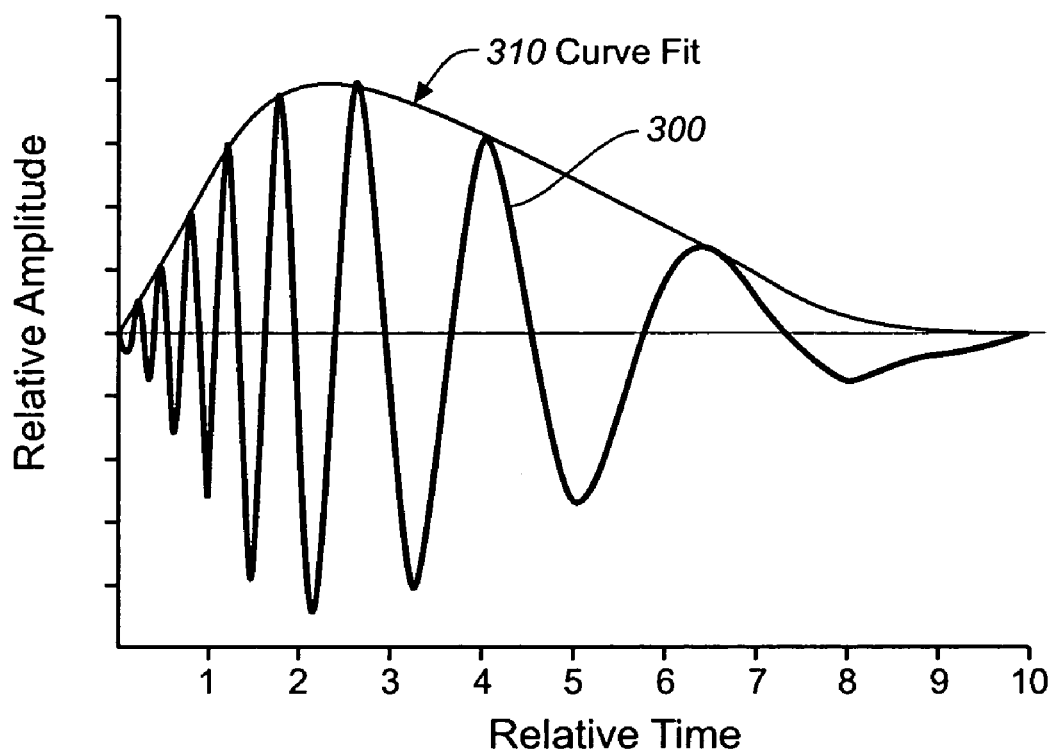

Once the wave characteristics of the oscillating free surface of the liquid have been detected or recorded, analysis of the echo data can begin. Examples of echo data for an oscillating free surface as it relaxes are shown in FIGS. 5a–5c.

The echo data or profiles may be analyzed or characterized in various ways. In one embodiment, an attribute (e.g., "$\Delta t$") may be defined and used to characterize the echo profile. The $\Delta t$ shown in FIGS. 5a–5b is the distance along the horizontal axis where the upper peak maxim value (UP) and the lower peak maxim value (LP) intersect the horizontal axis. $\Delta t$ corresponds to the viscosity-surface tension product of a liquid and varies with liquids having different viscosity and surface tensions.

After obtaining $\Delta t$ for a sample liquid having an unknown viscosity and surface tension, the sample liquid's viscosity-surface tension information may be identified by comparing its $\Delta t$ with candidate values contained in a library or database. The candidate values have known properties including, for example, wave dampening rates for a given acoustic stimuli, viscosity and surface tension information, density information, droplet ejection in response to certain acoustic stimuli, and other properties which may be useful in acoustic droplet ejection. Thus, by analyzing the source liquid in accordance with the foregoing, various information about the source liquid is obtained including its viscosity and surface tension information.

Curve fitting is another suitable technique to select or identify a candidate liquid. FIG. 5c shows the echo data 300 having a curve fit 310. Curve fit 310 may be estimated as a polynomial and matched with a candidate having a similar polynomial. The matching algorithms that can be used for this purpose range from simple least squares approach (linear regression) to a neural network-based approach as well as other curve fitting techniques. Such methods are discussed in various text books including Chapter 14 of "Mathematical Statistics and Data Analysis" by John Rice, Duxbury Press and Chapter 4 of "Neural Networks for Pattern Recognition" by Christopher Bishop, Oxford University Press. Accordingly, a sample liquid can be analyzed using the above described technique to obtain its viscosity and surface tension information without contacting the liquid.

Notwithstanding the above, there may be situations when data from a sample does not correlate with any candidate. In this situation, where known data fitting techniques do not provide a solution, the properties of two candidates having faster and slower dampening profiles (or attributes) may be averaged to predict or estimate the viscosity/surface tension product for the sample liquid. In another variation, the system may simply default to a predetermined viscosity surface tension product when the library does not provide an appropriate candidate. Still other data fitting and matching techniques may be utilized as is known to those skilled in the art.

The measuring technique provided by the present invention has various useful applications. An exemplary application of the present invention is to optimize droplet ejection based on measuring the product of the viscosity and surface tension of the liquid to be ejected. An acoustic ejector (e.g., the acoustic ejector 5 of FIG. 2) may be optimized by determining an optimal amount of energy (an acoustic stimuli) to be applied to eject a droplet 50 of liquid. Various parameters have been observed to affect droplet ejection including viscosity and surface tension information. It follows that by measuring the viscosity and surface tension information (e.g., the product) of the source liquid prior to ejection, the acoustic stimuli can be adjusted to compensate for liquids having various surface tensions and viscosity which would otherwise decrease the accuracy of the droplet ejection.

The viscosity and surface tension information, for example, can be supplied to the computer 95 and statistically compared with measured data to best estimate what energy should be applied to achieve a desired droplet. Suitable algorithms include maximum likelihood algorithms. Such algorithms determine the power which will most likely provide a desired droplet feature based on past data. Examples of droplet features or characteristics include size, mass, angle of ejection, spray threshold, etc.

Suitable algorithms for determining optimal values are known and can be found in various known texts. It is also to be understood that other information may used to determine an optimal power. Indeed, user input, density, liquid level, and other parameters may be input into an algorithm to determine the optimal power output. Furthermore, as each droplet is ejected, a database is updated with new information. The information is fed back to the computer to provide a better setting for subsequent droplet ejection.

Figure 1C:
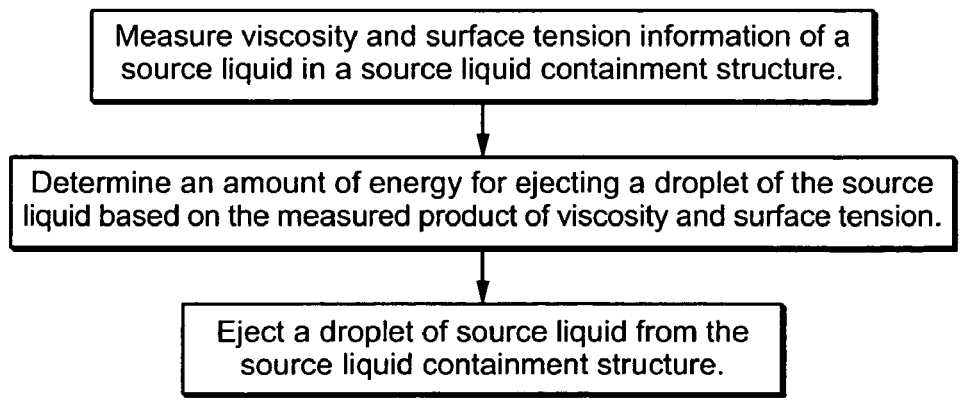
FIG. 1c is a block diagram illustrating the steps performed in a variation of the present invention to acoustically eject a droplet of source liquid based on measuring viscosity and surface tension information of the source liquid.

The steps of an acoustic ejector that utilize the viscosity and surface tension information of the present invention are shown in FIG. 1c. First, the viscosity and surface tension product are measured. Next, an optimized acoustic stimuli is determined based on the viscosity and surface tension information. The optimized acoustic stimuli is determined by comparing the measured product with past measured values of actual droplets ejected. A feedback algorithm is preferably employed to continuously optimize droplet ejection as more information is obtained.

Examples of liquids to be ejected include water, mixtures, solutions, solder, photoresists, biological compounds, and other substances which can be ejected or deposited onto a target substrate 80. Preferably, the acoustic ejector is used to eject liquids useful in biological or chemical applications.

The preceding examples are intended to illustrate but not to limit the invention in any manner, shape, or form, either explicitly or implicitly. While they are typical of those that might be used, other procedures, methodologies, or techniques known to those skilled in the art may alternatively be used.

While the invention has been described in detail with reference to certain preferred embodiments thereof, it will be understood that modifications and variations are within the spirit and scope of that which is described and claimed.

What is claimed is:

1. A non-contact method for measuring viscosity and surface tension information of a first liquid in a first liquid containment structure comprising the steps of:
   oscillating a free surface of the first liquid in the first liquid containment structure;
   detecting first liquid wave characteristics of the oscillating free surface;
   analyzing the first liquid wave characteristics to determine the viscosity and surface tension information; and
   wherein the oscillating step is performed by propagating an acoustic wave from an acoustic wave emitter, through said liquid containment structure, towards the free surface.

2. The method of claim 1 wherein the detecting step is performed by delivering a series of acoustic pulses at the free surface and detecting acoustic reflections from the free surface as the oscillating free surface relaxes.

3. The method of claim 2 wherein the series of acoustic pulses are synchronously phased.

4. The method of claim 2 wherein the series of acoustic pulses are emitted by the acoustic wave emitter used to cause the free surface to oscillate.

5. The method of claim 4 wherein the reflections are detected by the acoustic wave emitter used to cause the free surface to oscillate.

6. The method of claim 5 wherein the acoustic wave emitter comprises only one piezoelectric transducer for generation and detection of acoustic energy waves.

7. The method of claim 1 wherein said acoustic wave emitter is moveable relative to the containment structure.

8. The method of claim 1 wherein the containment structure is detachable from the emitter.

9. A non-contact method for measuring viscosity and surface tension information of a first liquid in a first liquid containment structure comprising the steps of:
   oscillating a free surface of the first liquid in the first liquid containment structure;
   detecting first liquid wave characteristics of the oscillating free surface;
   analyzing the first liquid wave characteristics to determine the viscosity and surface tension information; and
   wherein the containment structure is a multi-well plate.

10. A non-contact method for measuring viscosity and surface tension information of a first liquid in a first liquid containment structure comprising the steps of:
   oscillating a free surface of the first liquid in the first liquid containment structure;
   detecting first liquid wave characteristics of the oscillating free surface;
   analyzing the first liquid wave characteristics to determine the viscosity and surface tension information; and
   wherein said analyzing step comprises comparing the first liquid wave characteristics with candidate liquid wave characteristics wherein at least one attribute of the first liquid wave characteristics is compared to a corresponding attribute of the candidate liquid wave characteristics.

11. The method of claim 10 wherein said at least one attribute is a Δt defined by the time difference between an upper peak maxim value and lower peak maxim value of the first liquid wave characteristics.

12. A non-contact method for measuring viscosity and surface tension information of a first liquid in a first liquid containment structure comprising the steps of:
   oscillating a free surface of the first liquid in the first liquid containment structure;
   detecting first liquid wave characteristics of the oscillating free surface;
   analyzing the first liquid wave characteristics to determine the viscosity and surface tension information; and
   wherein the first liquid is selected from the group consisting of photoresist, solder, and a biological compound.

13. A method for acoustically ejecting a droplet of a first liquid from a first liquid containment structure comprising the steps of:
   measuring viscosity and surface tension information of the first liquid in the first liquid containment structure; and
   directing a variable amount of acoustic energy through the first liquid to cause the droplet ejection wherein the variable amount of acoustic energy is based on the measuring viscosity and surface tension information of the first liquid in the first liquid containment structure and wherein said measuring viscosity and surface information is performed by oscillating a free surface of the first liquid in the first liquid containment structure, detecting first liquid wave characteristics of the oscillating free surface, and analyzing the first liquid wave characteristics to determine the viscosity and surface tension information.

14. An apparatus for measuring viscosity and surface tension information of a first liquid in a first liquid containment structure comprising:
   an acoustic energy emitter; and
   a computer, which is in communication with said acoustic energy emitter, is configured to control said acoustic energy emitter to deliver a first acoustic energy pulse to disturb a free surface of the first liquid in the first liquid containment structure causing said free surface to oscillate, said computer is further configured to control said acoustic energy emitter to deliver a series of acoustic energy pulses at the oscillating free surface while the oscillating free surface is relaxing and said acoustic energy emitter being further configured to detect wave characteristics of the oscillating free surface by detecting echo signals from the series of energy pulses reflecting off the oscillating free surface, said computer is further configured to record said echo signals to determine said viscosity and surface tension information.

15. The apparatus of claim 14 wherein the acoustic wave emitter is configured to deliver an acoustic ejecting pulse sufficient to eject one or more droplets of liquid from said first liquid.

16. The apparatus of claim 14 wherein said acoustic energy emitter includes only one piezoelectric element to generate and detect acoustic energy to and from the free surface of said first liquid.

17. A system for acoustically ejecting a droplet of liquid from a first liquid containment structure comprising:
   an apparatus as recited in claim 14; and
   a stage for supporting the liquid containment structure wherein the stage is at least one of moveable and detachable relative to the acoustic energy emitter.

18. The apparatus of claim 14 wherein said computer is further configured to direct said acoustic energy emitter to transmit a variable amount of acoustic energy through the first liquid to cause a droplet ejection, wherein the variable amount of acoustic energy is based on said viscosity and surface tension information.

19. A non-contact method for measuring viscosity and surface tension information of a first liquid in a first liquid containment structure comprising the steps of:
   oscillating a free surface of the first liquid in the first liquid containment structure by propagating a focused acoustic wave from an acoustic wave emitter, through said liquid containment structure, then through said first liquid, towards the free surface;
   delivering a series of acoustic energy pulses at the oscillating free surface while the oscillating free surface is relaxing;
   detecting first liquid wave characteristics of the oscillating free surface by detecting echo signals from the series of energy pulses reflecting off the oscillating free surface; and
   analyzing the first liquid wave characteristics to determine the viscosity and surface tension information.

20. The method of claim 19 wherein said analyzing step comprises comparing the first liquid wave characteristics with candidate liquid wave characteristics wherein at least one attribute of the first liquid wave characteristics is compared to a corresponding attribute of the candidate liquid wave characteristics.

21. The method of claim 20 wherein said at least one attribute is at defined by the time difference between an upper peak maxim value and lower peak maxim value of the first liquid wave characteristics.

22. A method for acoustically ejecting a droplet of a first liquid from a first liquid containment structure comprising the steps of:
   measuring viscosity and surface tension information of the first liquid in the first liquid containment structure; and
   directing a variable amount of acoustic energy through the first liquid to cause the droplet ejection wherein the variable amount of acoustic energy is based on the measuring viscosity and surface tension information of the first liquid in the first liquid containment structure and wherein said measuring viscosity and surface information is performed as described in claim 19.

* * * * *